United States Patent [19]

D'Amico et al.

[11] 4,416,687

[45] Nov. 22, 1983

[54] 3,5-BIS (TRIFLUOROMETHYL)PHENOXY CARBOXYLIC ACIDS AND DERIVATIVES THEREOF

[75] Inventors: John J. D'Amico; Tann R. Schafer, both of Creve Coeur, Mo.

[73] Assignee: Monsanto Company, St. Louis, Mo.

[21] Appl. No.: 344,652

[22] Filed: Feb. 1, 1982

[51] Int. Cl.³ ............................................. E05B 59/00
[52] U.S. Cl. ........................................ 71/109; 71/108; 71/116; 71/118; 560/62; 562/472; 564/175
[58] Field of Search .......................... 560/62; 562/472; 71/108, 109, 116, 118

[56] References Cited

U.S. PATENT DOCUMENTS 3,894,074  7/1975  Wagner ................................ 560/62

FOREIGN PATENT DOCUMENTS 2024213  1/1980  United Kingdom ................... 560/62

Primary Examiner—Paul J. Killos
Attorney, Agent, or Firm—Stanley M. Tarter; Howard C. Stanley

[57] ABSTRACT

3,5-Bis (trifluoromethyl)phenoxy carboxylic acids and derivatives thereof have been found to reduce herbicidal injury of certain food crops, especially grain sorghum, due to the application thereto of herbicides that kill or control weeds that impede the yield of the crops.

13 Claims, No Drawings

3,5-BIS (TRIFLUOROMETHYL)PHENOXY CARBOXYLIC ACIDS AND DERIVATIVES THEREOF

This invention relates to novel and useful 3,5-bis-(trifluoromethyl)phenoxy carboxylic acids and derivatives thereof, as well as their use in compositions and methods for reducing injury to crop plants by herbicides, which comprises treating the crop plant locus or seed of the crop plant with an effective safening amount of 3,5-bis-(trifluoromethyl)phenoxy carboxylic acid or derivatives thereof as will be described more fully below. Seeds coated with such acids and derivatives are also within the present invention.

BACKGROUND OF THE INVENTION

Herbicides are very useful for controlling certain weeds and unwanted grasses in the presence of growing crops. However, many of the herbicides injure certain crop plants by slowing growth and development at application rates necessary to stunt or kill the weeds and grasses. Accordingly, many herbicides cannot be used for controlling weeds in the presence of certain crops. Obviously, a safening agent (also referred to as herbicide antidote) consisting of a composition that can be used to treat the seed of the crop plant, the crop plant locus or the crop plant itself, resulting in a reduction of injury due to application of the herbicide without an unacceptable corresponding reduction of herbicidal action on the weeds or grasses, would be quite beneficial. A new class of safening agents for doing that is provided by the present invention.

PRIOR ART

In U.S. Pat. No. 3,617,245 it is disclosed that m-trifluoromethylphenoxyacetic acid, its salts and its esters, are useful in controlling the height of rice plants by applying such chemical to the plants themselves. There is no disclosure or suggestion in this prior art patent of employing bis(trifluoromehtyl)phenoxy carboxylic acids and certain derivatives thereof as disclosed herein to protect grain sorghum seeds and the like from injury due to the use of a herbicide to kill or control the weeds and grasses that would interfere with the yield of grain sorghum. On the contrary, it has been found m-trifluoromethylphenoxyacetic acid and derivatives thereof are herbicidal in nature and do not protect grain sorghum seeds against the adverse effect of certain known herbicides. Therefore, it is quite surprising that the 3,5 bis (trifluoromethylphenoxy)carboxylic acid compounds of the present invention safen grain sorghum seeds against such known herbicides.

Phenoxy compounds generally are considered excellent for use as a chemical means to control weeds. For example, 2,4-dichlorophenoxyacetic acid (2,4-D) and 2,4,5-trichlorophenoxyacetic acid (2,4,5-T) are well known herbicides. Surprisingly, it has been found that the phenoxy compounds of the present invention function to protect crop seeds against the adverse effect of herbicides.

DESCRIPTION OF THE INVENTION

In accordance with the novel aspects of the present invention, injury to crop plants, such as corn, soybeans and especially injury to grain sorghum due to application thereto of herbicides, especially to herbicides of 2,3,3-trichloroallyl diisopropylthiocarbamate (whose common name is triallate),cis- and trans- 2,3-dichloroallyl diisopropylthiocarbamate (whose common name is diallate) and more especially acetanilide herbicides such as 2-chloro-2',6'-diethyl-N-(methoxymethyl)acetanilide (whose common name is alachlor); (2-chloro-2',6'-diethyl-N-(butoxymethyl)acetanilide (whose common name is butachlor); 2-chloro-N-isopropylacetanilide (whose common name is propachlor); N-(ethoxymethyl)-N-(2-ethyl-6-methyl-1-cyclohexen-1-yl)-2-chloroacetamide, N-(ethoxymethyl)-N-(2,5-dimethyl-1-cyclopenten-1-yl)-2-chloroacetamide; 2-chloro-N-(2-methoxy-1-methylethyl)-6'-ethyl-o-acetotoluidide; 2-chloro-N-(ethoxymethyl)-6'-ethyl-o-acetotoluidide (whose common name is acetachlor); ethyl ester of N-chloro-acetyl-N-(2,6-diethylphenyl) glycine; and 2-chloro-2',3'-dimethyl-N-(isopropyl)acetanilide; 2-chloro-2',6'-diethyl-N-(pyrazolylmethyl)acetanilide; 2-chloro-6'-trifluoromethyl-N-(isopropoxymethyl) acetanilide; 2-chloro-2'-methyl-6'-trifluoromethyl-N-(isopropoxymethyl)acetanilide; 2-chloro-2'-methyl-6'-trifluoromethyl-N-(ethoxymethyl)acetanilide; 2-chloro-2'-methyl-6'-methoxy-N-(isopropoxymethyl)acetanilide; 2-chloro-2'-methyl-6'-methoxy-N-(propoxymethyl)acetanilide; 2-chloro-2'-isobutoxy-6'-methyl-N-(propoxymethyl)-acetanilide; 2-chloro-2'-isobutoxy-6'-ethyl-N-(ethoxymethyl) acetanilide; and 2-chloro-2'-methyl-6'-ethoxy-N-(propoxymethyl)acetanilide may be reduced without a corresponding reduction in injury to the weeds by application to the crop plant locus or the seed of the crop plant prior to planting of an effective amount of a safening agent comprising a 3,5-bis(trifluoromethyl)phenoxy carboxylic acid or derivatives thereof having the structural formula:

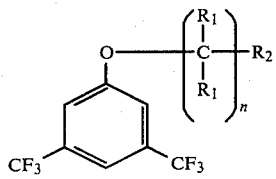

wherein $R_1$ is independently selected from the group consisting of hydrogen and $C_1$-$C_5$ alkyl, n is a whole number of 1-5, inclusive, and $R_2$ is selected from its group consisting of:

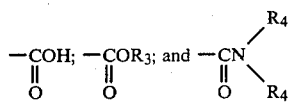

$R_3$ is selected from the group consisting of $C_1$-$C_5$ alkyl and agriculturally acceptable cations such as alkali metal cations and $R_4$ is independently selected from the group consisting of hydrogen and $C_1$-$C_5$ alkyl.

The amount of safening agent employed in the methods and compositions of the invention will vary depending upon the particular herbicide with which the agent is employed, the rate of application of the herbicide, the particular food crop seed to be protected, and the manner of application and use of the safening agent. In each instance the amount of agent employed is a safening effective amount, i.e., the amount which reduces or protects against crop injury that otherwise would result from the application of the herbicide. Furthermore, the amount of safening agent employed will be less than an amount that will substantially injure the crop seed.

The safening agent can be applied to the crop plant seed locus in a mixture with the selected herbicide. For example, where the crop seed is first planted, a suitable mixture of safening agent and herbicide whether in a homogenous liquid, emulsion, suspension or solid form can be topically applied to the surface of or incorporated in the soil in which the seeds have been planted. The herbicide will reduce or eliminate the presence of undesirable weed and grass plants. Where the herbicide would by itself injure the crop seeds, the presence of the safening agent will reduce or eliminate the injury to the crop seeds otherwise ensuing from the application of herbicide. It will be appreciated that it is not essential that the application of herbicide and the safening agent to the plant locus be made using the selected herbicide and safening agent in the form of a mixture or composition. The herbicide and the safening agent may be applied to the plant locus in a sequential manner. For example, the safening agent may be first applied to the plant locus and thereafter the herbicide is applied. The reverse order of the application of the safening agent and herbicide is also within the purview of the present invention. In such case the herbicide is first applied to the plant locus and thereafter the safening agent is applied. From an economic standpoint the safening agent and herbicide will normally be applied as a mixture, thus avoiding the expense of a dual application.

Furthermore, the application of the safening agent can be made directly on the seed before planting. In this practice, a quantity of crop seeds is first coated with the safening agent. The coated seeds are thereafter planted. Then, the herbicide is topically applied to soil in which the precoated seeds have been planted. This procedure is preferred where the cost of the safening agent is a determining factor.

By application to the "plant locus" is meant application to the plant growing medium, such as soil, as well as the seeds, emerging seedlings, roots, stems, leaves, flowers, fruits or other plant parts.

The amount of herbicide employed is well within the skill of the art and is disclosed in various patents. Propachlor and its herbicidal use is disclosed in U.S. Pat. No. 2,863,752 and U.S. Pat. Re. 26,961. Alachlor, butachlor and acetochlor and their herbicidal use are disclosed in U.S. Pat. Nos. 3,442,945 and 3,547,620. U.S. Pat. No. 3,937,730 discloses and claims 2-chloro-N-(2-methoxy-1-methylethyl)-6'-ethyl-o-acetototulidide. The herbicidal use of N-(ethoxymethyl)-N-(2-ethyl-6methyl-1-cyclohexen-1-yl)-2-chloracetamide and N-(ethoxymethyl)-N-2(2,5-dimethyl-1-cyclopenten-1-yl)-2-chloracetamide is disclosed in application Ser. No. 897,472, filed Apr. 18, 1978 by John P. Chupp.

The herbicidal use of 2-chloro-6'-trifluoromethyl-N-(isopropoxymethyl)acetanilide, 2-chloro-2'-methyl-6'-trifluoromethyl-N-(ethoxymethyl)acetanilide and 2-chloro-2'-methyl-6'-trifluoromethyl-N-(isopropoxymethyl)acetanilide is disclosed in application Ser. No. 133,718, filed Mar. 25, 1980 by John P. Chupp. The herbicidal use of 2-chloro-2'-methyl-6'-methoxy-N-(isopropoxymethyl)acetanilide, 2-chloro-2'-methyl-6'-methoxy-N-(propoxymethyl) acetanilide and 2-chloro-2'-methyl-6'-ethoxy-N-(propoxymethyl)acetanilide is disclosed in application Ser. No. 133,695 filed Mar. 25, 1980 by Gerhard H. Alt.

The method of preparing the phenoxy compounds of the present invention comprises reacting 3,5-ditrifluoromethylphenol under basic conditions with a compound of the general formula:

R—X wherein R has the structural formula

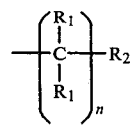

wherein $R_1$ is independently selected from the group consisting of hydrogen and $C_1$–$C_5$ alkyl, n is a whole number of 1–5 inclusive, $R_2$ is selected from the group consisting of

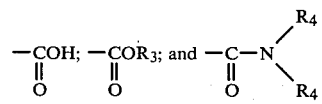

wherein $R_3$ is a $C_1$–$C_5$ alkyl and $R_4$ is independently selected from the group consisting of hydrogen and $C_1$–$C_5$ alkyl; and wherein X is a halogen including bromine, chlorine and iodine. The synthesis is preferably performed in a basic aqueous medium or organic solvent. The preferred base is potassium hydroxide. The reaction is conducted at a temperature of from 0° C. to about 100° C. or higher. Reaction times typically range from one hour to 72 hours, depending on the temperature, reactants, etc. The desired phenoxy compound is separated from the reaction mixture. To recover the amides and esters separation can conveniently be accomplished by cooling the reaction medium to a temperature sufficiently low to cause precipitation of the phenoxy compound. In the case of recovering the phenoxy acids, the medium should be acidified through the use of a strong mineral acid, such as hydrochloric acid, before precipitation is accomplished.

All the compounds used as starting materials in the synthesis of the compounds of this invention are commercially available, or can be prepared by known procedures in the chemical literature.

Useful organic solvents include acetone, N,N-dimethylformamide, N,N-dimethylacetamide, benzene, toluene, ethanol, isopropanol, and any other useful inert reaction solvent. An acid scavenger such as triethylamine or similar basic material can be used to absorb the hydrogen halide (e.g., HCl) liberated by the reaction. The reaction also goes well in basic aqueous media. The base used can be sodium hydroxide, potassium hydroxide, sodium carbonate, potassium carbonate, etc.

The reaction temperatures may be varied from 0° C. to about 100° C. or even higher when pressurized equipment is used. It is most convenient to run the reaction at the reflux temperature of the reaction mixture. Little or no side reactions or thermal degradations result from conducting the reactions at elevated temperatures.

In general, the reactions approach completion at rates dependent on the temperature. Thus, the speed of reaction can be increased by using a reaction solvent and operating at reflux temperature.

The most preferred compound of the invention is [3,5-bis-(trifluoromethyl)phenoxy]acetic acid.

In order to illustrate the manner in which the 3,5-bis-(trifluoromethyl)phenoxy compounds of the present invention are prepared, the following examples are provided.

EXAMPLE 1

Preparation of [3,5-bis(trifluoromethyl)phenoxy]acetic acid

To a stirred solution containing 115 g (0.50 mole) of 3,5-ditrifluoromethylphenol, 44 g (0.55 mole) of 50% aqueous sodium hydroxide and 500 ml of water, 76.4 g (0.55 mole) of bromoacetic acid in 250 ml of water neutralized with 38.7 g of potassium carbonate to pH=9 was added in one portion. The stirred reaction mixture was heated at 80°–90° C. for 24 hours. After cooling to 0° C., 60 g (0.60 mole) of concentrated hydrochloric acid in 500 ml of water was added dropwise to the solution. After stirring at 0°–10° C., the resulting solid was collected by filtration, washed with water until the washings were neutral to litmus and air-dried at 25°–30° C. A product with a melting point of 103°–104° C. was obtained in 80% yield.

Analysis Calculated for $C_{10}H_6F_6O_3$: C, 41.68%; H, 2.10%. Found: C, 41.81%; H, 2.19%.

EXAMPLE 2

Preparation of ethyl 2-[3,5-bis(trifluoromethyl)phenoxy]propionate

To a stirred solution containing 17.3 g (0.075 mole) of 3,5-ditrifluoromethylphenol, 5 g (0.075 mole) of 85% potassium hydroxide, 150 ml of dimethylformamide and 7 ml of water, 14.6 g (0.08 mole) of ethyl 2-bromopropionate was added in one portion. The stirred reaction mixture was heated at 80°–90° C. for 24 hours. After cooling to 25° C., 500 ml of water and 500 ml of ethyl ether were added and stirring was continued for 15 minutes. The separated ether layer was washed with water until neutral to litmus and dried over sodium sulfate. The ether was removed in vacuo at maximum temperature of 50°C. at 1–2 mm of Hg. The resulting product was obtained as an amber liquid, $N_D^{25}=1.4184$ in 97% yield.

Analysis Calculated for $C_{13}H_{12}F_6O_3$: C, 47.28%, H, 3.66%. Found: C, 47.32%; H, 3.70%.

EXAMPLE 3

Preparation of 2-[3,5-bis(trifluoromethyl)phenoxy]propionic acid

A stirred charge containing 0.05 mole of ethyl-2-[3,5-bis-(trifluoromethyl)phenoxy]propionate, 150 ml of ethyl alcohol, 8 g (0.1 mole) of 50% aqueous solution of sodium hydroxide and 25 ml of water was heated at reflux for 5 hours and at 25°–30° C. for 18 hours. After cooling to 5° C. 800 ml of water containing 15 g (0.15 mole) of concentrated hydrochloric acid was added slowly. After stirring at 0°–10° C. for one hour, the resulting solid was collected by filtration, washed with cold water and air-dried at 25°–30° C. A product with a melting point of 51°–53° C. was obtained with a yield of 97%.

Analysis Calculated for $C_{11}H_8F_6O_3$: C, 43.72%; H, 2.67%. Found: C, 43.87%, H, 2.68%.

EXAMPLE 4

Preparation of 4-[3,5-bis(trifluoromethyl)phenoxy]-butanoic acid

A stirred charge containing 0.05 mole of ethyl-4-[3,5-bis-(trifluoromethyl)phenoxy]butyrate, 150 ml of ethyl alcohol, 8 g (0.1 mole) of 50% aqueous solution of sodium hydroxide and 25 ml of water was heated at reflux for 5 hours and at 25°–30° C. for 18 hours. After cooling to 5° C., 800 ml of water containing 15 g (0.15 mole) of concentrated hydrochloric acid was added slowly. After stirring at 0°–10° C. for one hour, the resulting solid was collected by filtration, washed with cold water and air dried at 25°–30° C. A product with a melting point of 85°–87° C. was obtained with a yield of 87%.

Analysis Calculated for $C_{12}H_{10}F_6O_3$: C, 45.58%; H, 3.19%. Found: C, 45.47%; H, 3.21%.

EXAMPLE 5

Preparation of ethyl [3,5-bis(trifluoromethyl)phenoxy]acetate

To a stirred solution containing 11.5 g (0.05 mole) of 3,5-ditrifluoromethylphenol, 3.3 g (0.05 mole) of 85% potassium hydroxide, 200 ml of N,N-dimethylformamide and 10 ml of water, 0.055 mole of ethyl bromoacetate was added in one portion. The stirred reaction mixture was heated at 80°–90° C. for 46 hours. After cooling 25° C., 500 ml of water and 500 ml of ethyl ether were added; and stirring was continued for 15 minutes. The separated ether layer was washed with water until neutral to litmus and dried over sodium sulfate. The ether was removed in vacuo at a maximum temperature of 80°–90° C. at 1–2 mm of Hg. A product was obtained with $N_D^{25}$ of 1.4226 with a yield of 85%.

Analysis Calculated for $C_{12}H_{10}F_6O_5$: C, 45.58%; H, 3.19%. Found: C, 45.35%, H, 3.21%.

EXAMPLE 6

Preparation of methyl [3,5-bis(trifluoromethyl)phenoxy]acetate

To a stirred solution containing 11.5 g (0.05 mole) of 3,5-ditrifluoromethylphenol, 3.3 g (0.05 mole) of 85% potassium hydroxide, 200 ml of N,N-dimethylformamide and 10 ml of water, 0.055 mole of methyl bromoacetate was added in one portion. The stirred reaction mixture was heated at 80°–90° C. for 22 hours. After cooling to 25° C., 500 ml of water and 500 ml of ethyl ether were added; and stirring was continued for 15 minutes. The separated ether layer was washed with water until neutral to litmus and dried over sodium sulfate. The ether was removed in vacuo at a maximum temperature of 80°–90° C. at 1–2 mm of Hg. A product with a melting point of 65°–67° C. (after recrystallization from heptane) was obtained with a yield of 99%.

Analysis Calculated for $C_{11}H_8F_6O_3$: C, 43.72%, H, 2.67%. Found: C, 43.58%; H, 2.67%.

EXAMPLE 7

Preparation of ethyl 4-[3,5-bis(trifluoromethyl)phenoxy]butyrate

To a stirred solution containing 11.5 g (0.05 mole) of 3,5-ditrifluoromethylphenol, 3.3 g (0.05 mole) of 85% potassium hydroxide, 200 ml of N,N-dimethylformamide and 10 ml of water, 0.055 mole of ethyl 4-bromobutyrate was added in one portion. The stirred reaction mixture was heated at 80°–90° C. for 24 hours. After cooling to 25° C., 500 ml of water and 500 ml of ethyl ether were added; and stirring was continued for 15 minutes. The separated ether layer was washed with water until neutral to litmus and dried over sodium sulfate. The ether was removed in vacuo at a maximum temperature of 80°–90° C. at 1–2 mm of Hg. A product with a $N_D^{25} = 1.4281$ was obtained with a 95% yield.

Analysis Calculated for $C_{14}H_{14}F_6O_3$: C, 48.84%; H, 4.10%. Found: C, 48.86%; H, 4.14%.

EXAMPLE 8

Preparation of 2-[3,5-bis(trifluoromethyl)phenoxy]acetamide

To a stirred solution containing 5 g (0.022 mole) of 3,5-ditrifluoromethylphenol, 1.6 g (0.024 mole) of 85% potassium hydroxide, 10 ml of water and 200 ml of acetone, 0.024 mole of chloroacetamide was added in one portion. The stirred reaction mixture was heated at 56°–60° C. for 22 hours. After cooling to 0° C., 600 g of ice water was added and stirring continued at 0°–10° C. for 30 minutes. The resulting solid was collected by filtration, washed with water until neutral to litmus and air dried at 25°–30° C. A product with a melting point of 139°–141° C. (determined after recrystallization from 6:1 mixture of heptane and isopropyl alcohol) was obtained with a 32% yield.

Analysis Calculated for $C_{10}H_7F_6NO_2$: C, 41.83%; H, 2.46%; N, 4.88%. Found: C, 41.87%; H, 2.49%; N, 4.87%.

EXAMPLE 9

Preparation of N-methyl 2-[3,5-bis(trifluoromethyl)phenoxy]acetamide

To a stirred solution containing 5 g (0.022 mole) of 3,5-ditrifluoromethylphenol, 1.6 g (0.024 mole) of 85% potassium hydroxide, 10 ml of water and 200 ml of acetone, 0.024 mole of N-methyl chloroacetamide was added in one portion. The stirred reaction mixture was heated at 56°–60° C. for 22 hours. After cooling to 0° C., 600 g of ice water was added and stirring continued at 0°–10° C. for 30 minutes. The resulting solid was collected by filtration, washed with water until neutral to litmus and air-dried at 25°–30° C. A product with a melting point of 98°–99° C. (determined after recrystallization from heptane) was obtained with a 24% yield.

Analysis Calculated for $C_{11}H_9F_6NO_2$: C, 43.87%, H, 3.01%; N, 4.65%. Found: C, 43.87%; H, 3.02%; N, 4.62%.

EXAMPLE 10

Preparation of 2-[3,5-bis(trifluoromethyl)phenoxy]propanamide

To a stirred solution containing 5 g (0.22 mole) of 3,5-ditrifluoromethylphenol, 1.6 g (0.024 mole) of 85% potassium hydroxide, 10 ml of water and 200 ml of N,N-dimethylformamide, 0.024 mole of 2-chloropropionamide was added in one portion. The stirred reaction mixture was heated at 120°–130° C. for 46 hours. After cooling to 0° C., 600 g of ice water was added and stirring continued at 0°–10° C. for 30 minutes. The resulting solid was collected by filtration, washed with water until neutral to litmus and air-dried at 25°–30° C. A product with a melting point of 84°–85° C. (determined after recrystallization from heptane) was obtained with a 48% yield.

Analysis Calculated for $C_{11}H_9F_6NO_2$: C, 43.87%; H, 3.01%; N, 4.65%. Found: C, 43.66%, H, 3.02%; N, 4.62%.

EXAMPLE 11

Preparation of the sodium salt of [3,5-bis(trifluoromethyl)phenoxy]acetic acid

A stirred charge containing 15.8 g (0.05 mole) of ethyl [3,5-bis(trifluoromethyl)phenoxy]acetate prepared in accordance with Example 5, 4 g (0.05 mole) of 50% aqueous sodium hydroxide, 200 ml of ethyl alcohol and 5 ml of water was heated at reflux for 5 hours and at 25°–30° C. for 19 hours. The ethyl alcohol and water were removed in vacuo at a maximum temperature of 80°–90° C. at 1–2 mm of Hg. The resulting solid was air-dried at 25°–30° C. The sodium salt was obtained in 95% yield.

Analysis Calculated for $C_{10}H_5F_6NaO_3$: C, 38.73%; H, 1.63%; Na, 7.41%; Found: C, 37.63%; H, 1.98%; Na, 7.16%.

In the following Examples, 12 through 24, the seed plantings and the sequential application of the herbicide and safening agents are accomplished in the following manner:

A good grade of fumigated silt loam top soil is placed in a container and compacted to a depth of approximately 1.27 cm. from the top of said container. A predetermined number of seeds of each of the crop species to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of the herbicide dispersed or dissolved in a suitable carrier is thereafter sprayed on the soil already treated with the safening agent. The soil containing the safening agent and/or herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and/or herbicide or with untreated soil, and the pots are leveled. The pots are then placed on a sand bench in the greenhouse and watered from below as needed. When the seeds are treated with safener, the application of the safener to the soil is omitted. The coated seeds are placed on top of the soil in the pot and the balance of the treatment procedure is the same. The plants are observed at the end of approximately 21 days and the results in terms of percent inhibition of growth are recorded. For each test series, a pot is also prepared containing no herbicide and no safening agent as a control. For each treatment, the herbicidal activity is observed on pots treated with the same quantity of herbicide alone. The results are observed and recorded as percent inhibition of each plant species tested. Safener formulations are prepared as solutions, emulsifiable concentrates or wettable powders. Appropriate amounts of seed are weighed and placed into the container of safener. The contents are then thoroughly mixed until all seeds are suitably coated. When safeners are used in powder form, the seeds may be planted immediately after treatment. When liquid safeners are used, the seeds are dried prior to planting. The amount of safener on the seeds is determined on a weight percent basis.

In the following specific examples, the tank mixes of herbicide, safener, or combination thereof were prepared by dissolving the appropriate amount of active ingredient in acetone. Where the seed is treated, the active ingredients were dissolved in methylene chloride.

name, and structure of the particular herbicide can be ascertained by reference to Table I.

TABLE I

| Herbicide Identification Number | Common Name | Chemical Structure | |
|---|---|---|---|
| H-1 | Triallate | $[(CH_3)CH]_2NCSCH_2C=C=Cl_2$ with Cl, and C=O | 2,3,3-trichloroallyldiisopropylthio-carbamate |
| H-2 | Atrazine | (triazine structure) | 2-chloro-4-ethylamino-6-isopropylamino-1,3,5-triazine |
| H-3 | Alachlor | $ClCH_2C(=O)-N-CH_2OCH_3$ with 2,6-diethylphenyl | 2-chloro-2',6'-diethyl-N—(methoxymethyl)-acetanilide |
| H-4 | Butachlor | $ClCH_2C(=O)-N-CH_2-O(CH_2)_3CH_3$ with 2,6-diethylphenyl | 2-chloro-2',6'-diethyl-N—(butoxymethyl)-acetanilide |
| H-5 | (not available) | $ClCH_2C(=O)-N-CH_2OC_3H_7$ with 2-methyl-6-methoxyphenyl | 2-chloro-2'-methyl-6'-methoxy-N—(isopropyl)acetanilide |

EXAMPLE 12

This Example shows the safening effect with respect to certain plants of ethyl 2-[3,5-bis(trifluoromethyl)-phenoxy]propionate prepared in accordance with Example 2 and whose chemical structure is as follows:

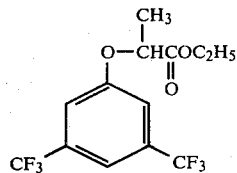

The crop seed identifications, together with the rates of application of herbicide in kilograms per hectare and the percent inhibition, are set forth in Table II. In the tables throughout the specification, an entry of NP means not planted and an entry of ND means no data.

The five known herbicides are identified as follows in Table I. Throughout the examples the particular herbicide will be identified by reference numbers such as H-1, H-2, etc. The particular chemical name, common The five herbicides and the safening compound of Example 12 were sequentially sprayed in separate treatments on the same spectrum of planted crop seeds and the percent inhibitions were noted. In Table II there are given data with respect to rates of application of the herbicides and the safening compound of Example 12. The percent inhibitions of the crop are also listed.

It can be seen from Table II that the safening compound of Example 12 significantly protects certain crops against the otherwise pernicious effect of the listed herbicides. For example, when Herbicide No. 2 (atrazine) was applied at a rate of 4.48 kg/h, the percent rice growth inhibition was 65. However, this inhibition was reduced to 45% when 8.96 kg/h of the safening compound of Example 12 was used to protect against the adverse effect of the herbicide. Even more significant is the fact that when Herbicide No. 3 (alachlor) was applied at the rate of 2.24 kg/h, the percent grain sorghum inhibition was reduced from 90 to 15 through the use of 8.96 kg/h of the safening compound Example 12.

Next, a treatment was run to show the safening effect of the compound of Example 12 when various amounts of Herbicide No. 3 (alachlor) were applied to various crop seeds using an application rate of 8.96 kg/h of safener. The results of these tests have been set forth in Table III.

TABLE II

| Herbicide No. | Rate of Herbicide, kg/h | Rate of Safener kg/h | % Plant Inhibition | | | | | |
|---|---|---|---|---|---|---|---|---|
| | | | Sugar Beet | Grain Sorghum | Wheat | Rice | Soybeans | Corn |
| 1 | 0.56 | 0 | NP | NP | 100 | NP | NP | NP |
| 2 | 4.48 | 0 | NP | NP | NP | 65 | 65 | NP |
| 3 | 2.24 | 0 | 90 | 90 | 70 | NP | NP | NP |

TABLE II-continued

| Herbicide No. | Rate of Herbicide, kg/h | Rate of Safener kg/h | % Plant Inhibition | | | | | |
|---|---|---|---|---|---|---|---|---|
| | | | Sugar Beet | Grain Sorghum | Wheat | Rice | Soybeans | Corn |
| 4 | 4.48 | 0 | NP | NP | NP | 80 | NP | NP |
| 5 | 2.24 | 0 | NP | NP | NP | NP | NP | 80 |
| 1 | 0.56 | 8.96 | NP | NP | 95 | NP | NP | NP |
| 2 | 4.48 | 8.96 | NP | NP | NP | 45 | 70 | NP |
| 3 | 2.24 | 8.96 | 100 | 15 | 65 | NP | NP | NP |
| 4 | 4.48 | 8.96 | NP | NP | NP | 90 | NP | NP |
| 5 | 2.24 | 8.96 | NP | NP | NP | NP | NP | NP |

TABLE III

| Herbicide No. | Rate of Herbicide, kg/h | Rate of Safener, kg/h | % Plant Inhibition | | | |
|---|---|---|---|---|---|---|
| | | | Sugar Beet | Grain Sorghum | Wheat | Green Foxtail |
| 3 | 4.48 | 0.0 | 90 | 95 | 90 | 100 |
| 2 | 2.24 | 0.0 | 90 | 90 | 70 | 100 |
| 3 | 1.12 | 0.0 | 80 | 40 | 30 | 100 |
| 3 | 0.56 | 0.0 | 80 | 40 | 30 | 100 |
| 3 | 4.48 | 8.96 | 100 | 30 | 95 | 100 |
| 3 | 2.24 | 8.96 | 90 | 10 | 70 | 100 |
| 3 | 1.12 | 8.96 | 70 | 0 | 70 | 100 |
| — | 0.56 | 8.96 | NP | 0 | 60 | 100 |
| — | 0 | 8.96 | 0 | 0 | 0 | 100 |

It is to be noted from Table III that when the safener of Example 12 is applied at a rate of 8.96 kg/h, the safening of grain sorghum against the pernicious effect of alachlor applied at various rates is most significant.

EXAMPLE 13

This example shows the safening effect with respect to certain plants of [3,5-bis(trifluoromethyl)phenoxy]acetic acid prepared in accordance with Example 1 and whose chemical structure is as follows:

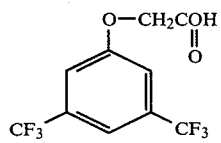

The five herbicides identified in Table I were sprayed in separate treatments on the surface of soil containing crop seeds and the percent growth inhibitions were determined. The crop identifications and the results thereof are set forth in Table IV.

TABLE IV

| Herbicide No. | Rate of Herbicide, kg/h | Rate of Safener, kg/h | % Plant Inhibition | | | | |
|---|---|---|---|---|---|---|---|
| | | | Grain Sorghum | Wheat | Rice | Soybean | Corn |
| 1 | 0.56 | 0 | NP | 100 | NP | NP | NP |
| 2 | 6.72 | 0 | NP | NP | 80 | 90 | NP |
| 3 | 2.24 | 0 | 90 | 85 | NP | NP | NP |
| 4 | 6.72 | 0 | NP | NP | 75 | NP | NP |
| 5 | 1.12 | 0 | NP | NP | NP | NP | 65 |
| 1 | 0.56 | 8.96 | NP | 100 | NP | NP | NP |
| 2 | 6.72 | 8.96 | NP | NP | 85 | 98 | NP |
| 3 | 2.24 | 8.96 | 30 | 70 | NP | NP | NP |
| 4 | 6.72 | 8.96 | NP | NP | 85 | NP | NP |
| 5 | 1.12 | 8.96 | NP | NP | NP | NP | 0 |

It can be seen from Table IV that the safening compound of Example 13 significantly protects certain crops against the otherwise pernicious effect of the listed herbicides. For example, when Herbicide No. 3 (alachlor) was applied at a rate of 2.24 kg/h, the percent grain sorghum growth inhibition was 90. However, this inhibition was reduced to 30% when 8.96 kg/h of the safening compound of Example 13 was used to protect against the adverse effect of the herbicide. Even more significant is the fact that when Herbicide No. 5 was applied at 1.12 kg/h, the percent corn inhibition was reduced from 65 to 0 through the use of 8.96 kg/h of the safening compound of Example 13.

Next, a treatment was run to show the safening effect of the compound of Example 13 when various amounts of Herbicide No. 3 (alachlor) were applied at a rate of 8.96 kg/h of safener. The results of this treatment have been set forth in Table V.

TABLE V

| Herbicide No. | Rate of Herbicide, kg/h | Rate of Safener kg/h | % Plant Inhibition | | | |
|---|---|---|---|---|---|---|
| | | | Sugarbeet | Grain Sorghum | Wheat | Green Foxtail |
| 3 | 0.56 | 8.96 | 90 | 20 | 20 | 97 |
| 3 | 1.12 | 8.96 | 100 | 10 | 60 | 97 |
| 3 | 2.24 | 8.96 | 95 | 10 | 50 | 98 |
| 3 | 4.48 | 8.96 | 99 | 30 | 80 | 98 |
| 3 | 0.56 | 0 | 50 | 10 | 20 | 90 |
| 3 | 1.12 | 0 | 50 | 40 | 50 | 98 |
| 3 | 2.24 | 0 | 60 | 60 | 70 | 95 |
| 3 | 4.48 | 0 | 70 | 75 | 75 | 99 |

TABLE V-continued

| Herbicide No. | Rate of Herbicide, kg/h | Rate of Safener kg/h | % Plant Inhibition | | | |
|---|---|---|---|---|---|---|
| | | | Sugarbeet | Grain Sorghum | Wheat | Green Foxtail |
| — | 0 | 8.96 | 0 | 0 | 0 | 0 |

It is noted from Table V that when the safener of Example 13 is applied at a rate of 8.96 kg/h, the safening of grain sorghum against the pernicious effect of alachlor applied at various rates of 1.12 kg/h or more is most significant.

EXAMPLE 14

This Example shows the safening effect with respect to certain plants of 4-[3,5-bis(trifluoromethyl)phenoxy]-butanoic acid prepared in accordance with Example 4 and whose chemical structure is as follows:

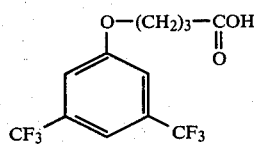

The five herbicides identified in Table I were sprayed in separate treatments on the surface of soil containing various crop seeds and the percent growth inhibitions were determined. The crop identifications and the results thereof are set forth in Table VI.

TABLE VI

| Herbicide No. | Rate of Herbicide, kg/h | Rate of Safener, kg/h | % Plant Inhibition | | | | | |
|---|---|---|---|---|---|---|---|---|
| | | | Sugar Beet | Grain Sorghum | Wheat | Rice | Soybean | Corn |
| 1 | 0.56 | 0 | NP | NP | 100 | NP | NP | NP |
| 2 | 4.48 | 0 | NP | NP | NP | 80 | 75 | NP |
| 3 | 2.24 | 0 | 95 | 65 | 75 | NP | NP | NP |
| 4 | 4.48 | 0 | NP | NP | NP | 75 | NP | NP |
| 5 | 2.24 | 0 | NP | NP | NP | NP | NP | 75 |
| 1 | 0.56 | 8.96 | NP | NP | 100 | NP | NP | NP |
| 2 | 4.48 | 8.96 | NP | NP | NP | 90 | 35 | NP |
| 3 | 2.24 | 8.96 | 95 | 10 | 75 | NP | NP | NP |
| 4 | 4.48 | 8.96 | NP | NP | NP | 90 | NP | NP |
| 5 | 2.24 | 8.96 | NP | NP | NP | NP | NP | 60 |

It can be seen from Table VI that the safening compound of Example 14 significantly protects certain crops against the otherwise pernicious effect of the listed herbicides. For example, when Herbicide No. 3 (alachlor) was applied at a rate of 2.24 kg/h, the percent grain sorghum growth inhibition was 65. However, this inhibition was reduced to 10% when 8.96 kg/h of the safening compound of Example 14 was used to protect against the adverse effect of the herbicide. Also significant is the fact that when Hericide No. 2 (atrazine) was used at 4.48 kg/h, the percent soybean inhibition was reduced from 75 to 35 through the use of 8.96 kg/h of the safening compound of Example 14.

Next a treatment was run to show the safening effect of the compound of Example 14 when various amounts of Herbicide No. 2 (atrazine) were applied at a rate of 8.96 kg/h of safener. The results of this treatment have been set forth in Table VII.

TABLE VII

| Herbicide No. | Rate of Herbicide, kg/h | Rate of Safener, kg/h | % Plant Inhibition | | | |
|---|---|---|---|---|---|---|
| | | | Rice | Soybean | Hemp Sesbania | Velvetleaf |
| 2 | 6.72 | 8.96 | 80 | 55 | 90 | 99 |
| 2 | 4.48 | 8.96 | 90 | 80 | 85 | 99 |
| 2 | 2.24 | 8.96 | 60 | 55 | 80 | 70 |
| 2 | 1.12 | 8.96 | 10 | 10 | 80 | 50 |
| 2 | 6.72 | 0 | 95 | 85 | 98 | 100 |
| 2 | 4.48 | 0 | 80 | 50 | 98 | 98 |
| 2 | 2.24 | 0 | 40 | 20 | 80 | 70 |
| 2 | 1.12 | 0 | 15 | 10 | 65 | 55 |
| — | 0 | 8.96 | 0 | 0 | 0 | 0 |

It is noted from Table VII that when the safener of Example 14 is applied at the rate of 8.96 kg/h, the safening of soybeans against the pernicious effect of atrazine applied at a rate of 6.72 kg/h is noted in two out of four treatments.

Next, a treatment was run to show the safening effect of the compound of Example 14 when various amounts of Herbicide No. 3 (alachlor) were applied at a rate of 8.96 kg/h of safener. The results of this treatment have been set forth in Table VIII.

TABLE VIII

| Herbicide No. | Rate of Herbicide kg/h | Rate of Safener kg/h | % Plant Inhibition | | | |
|---|---|---|---|---|---|---|
| | | | Sugar Beet | Grain Sorghum | Wheat | Green Foxtail |
| 3 | 4.48 | 8.96 | ND | 90 | 90 | 100 |
| 3 | 2.24 | 8.96 | 60 | 70 | 70 | 95 |
| 3 | 1.12 | 8.96 | 70 | 50 | 50 | 100 |
| 3 | 5.60 | 8.96 | ND | 30 | 15 | 99 |
| 3 | 4.48 | 0 | 80 | 99 | 85 | 99 |
| 3 | 2.24 | 0 | 80 | 98 | 85 | 99 |
| 3 | 1.12 | 0 | 60 | 90 | 70 | 99 |

TABLE VIII-continued

| Herbicide No. | Rate of Herbicide kg/h | Rate of Safener kg/h | % Plant Inhibition | | | |
|---|---|---|---|---|---|---|
| | | | Sugar Beet | Grain Sorghum | Wheat | Green Foxtail |
| 3 | 5.60 | 0 | 50 | 65 | 60 | 99 |
| — | 0 | 8.96 | 0 | 0 | 0 | 0 |

It is noted from Table VIII that when the safener of Example 14 is applied at the rate of 8.96 kg/h, the safening of sugar beets, grain sorghum and wheat against the pernicious effect of alchlor is seen.

EXAMPLE 15

This Example shows the safening effect with respect to certain plants of ethyl 4-[3,5-bis(trifluoromethyl)-phenoxy]butyrate prepared in accordance with Example 7 and whose chemical structure is as follows:

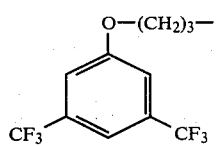

The five herbicides identified in Table I were sprayed in separate treatments on the surface of soil containing various crop seeds and the percent growth inhibitions were determined. The crop identifications and the results thereof are set forth in Table IX.

against the otherwise pernicious effect of the listed herbicides. When Herbicide No. 3 (alachlor) was applied at 2.24 kg/h, the percent grain sorghum inhibition was 95. However, this inhibition was reduced to 40% when 8.96 kg/h of the safening compound of Example 15 was used to protect against the adverse effect of the herbicide. Also, significant is the fact that when Herbicide No. 5 was used at 2.24 kg/h, the percent corn inhibition was reduced from 75 to 30 through the use of 8.96 kg/h of the safening compound of Example 15.

Next, a treatment was run to show the seed safening effect of the compound of Example 15 when various amounts of Herbicide No. 3 (alachlor) were applied at a rate of 8.96 kg/h of safener. The results of this treatment have been set forth in Table X.

TABLE X

| Herbicide No. | Rate of Herbicide, kg/h | Rate of Safener, kg/h | % Plant Inhibition | | | |
|---|---|---|---|---|---|---|
| | | | Sugar Beet | Grain Sorghum | Wheat | Green Foxtail |
| 3 | 4.48 | 8.96 | ND | 75 | 60 | 100 |
| 3 | 2.24 | 8.96 | 95 | 50 | 40 | 100 |
| 3 | 1.12 | 8.96 | 90 | 50 | 35 | 100 |
| 3 | 0.56 | 8.96 | 60 | 30 | 25 | 100 |
| 3 | 4.48 | 0 | 90 | 90 | 80 | 100 |
| 3 | 2.24 | 0 | 80 | 85 | 70 | 100 |
| 3 | 1.12 | 0 | 60 | 50 | 50 | 100 |
| 3 | 0.56 | 0 | 45 | 25 | 40 | 100 |
| — | 0 | 8.96 | 0 | 0 | 0 | 0 |

It is noted from Table X that when the seed safener of Example 15 is applied at the rate of 8.96 kg/h, the safening of grain sorghum against the pernicious effect of alachlor applied at certain rates is most significant.

Next, a treatment was run to show the safening effect of the compound of Example 15 when various amounts of Herbicide 5 were applied at a rate of 8.96 kg/h of safener. The results of this treatment have been set forth

TABLE IX

| Herbicide No. | Rate of Herbicide, kg/h | Rate of Safener, kg/h | % Plant Inhibition | | | | | |
|---|---|---|---|---|---|---|---|---|
| | | | Sugar Beet | Grain Sorghum | Wheat | Rice | Soybean | Corn |
| 1 | 0.56 | 0 | NP | NP | 100 | NP | NP | NP |
| 2 | 4.48 | 0 | NP | NP | NP | 75 | 80 | NP |
| 3 | 2.24 | 0 | 100 | 95 | 70 | NP | NP | NP |
| 4 | 4.48 | 0 | NP | NP | NP | 75 | NP | NP |
| 5 | 2.24 | 0 | NP | NP | NP | NP | NP | 75 |
| 1 | 0.56 | 8.96 | NP | NP | 85 | NP | NP | NP |
| 2 | 4.48 | 8.96 | NP | NP | NP | 80 | 90 | NP |
| 3 | 2.24 | 8.96 | 100 | 40 | 55 | NP | NP | NP |
| 4 | 4.48 | 8.96 | | NP | NP | 80 | NP | NP |
| 5 | 2.24 | 8.96 | NP | NP | NP | NP | NP | 30 |

It can be seen from Table IX that the safening compound of Example 15 significantly protects certain crop in Table XI.

TABLE XI

| Herbicide No. | Rate of Herbicide, kg/h | Rate of Safener, kg/h | % Plant Inhibition | | |
|---|---|---|---|---|---|
| | | | Green Foxtail | Barnyardgrass | Corn |
| 5 | 2.24 | 8.96 | 100 | 100 | 70 |
| 5 | 1.12 | 8.96 | 100 | 100 | 60 |
| 5 | 0.56 | 8.96 | 100 | 100 | 40 |
| 5 | 0.28 | 8.96 | 100 | 95 | 15 |
| 5 | 2.24 | 0 | 100 | 100 | 95 |
| 5 | 1.12 | 0 | 100 | 100 | 90 |
| 5 | 0.56 | 0 | 100 | 100 | 50 |

TABLE XI-continued

| Herbicide No. | Rate of Herbicide, kg/h | Rate of Safener, kg/h | % Plant Inhibition | | |
|---|---|---|---|---|---|
| | | | Green Foxtail | Barnyardgrass | Corn |
| 5 | 0.28 | 0 | 90 | 100 | 35 |
| — | 0 | 8.96 | 0 | 0 | 0 |

It is noted from Table XI that when the safener of Example 15 is applied at a rate of 8.96 kg/h, the safening of corn against the pernicious effect of Herbicide No. 5 is most significant. Furthermore, the safener does not reduce the effect of the herbicide against the undesirable weeds of green foxtail and barnyardgrass.

EXAMPLE 16

This Example shows the safening effect with respect to certain plants of 2-[3,5-bis(trifluoromethyl)phenoxy]-propionic acid prepared in accordance with Example 3 and whose chemical structure is as follows:

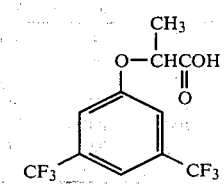

The five herbicides identified in Table I were sprayed in separate treatments on the surface of said containing various crop seeds and the percent growth inhibitions were determined. The crop identifications and the results thereof are set forth in Table XII.

Herbicide No. 2 (atrazine) was used at 4.48 kg/h, the percent soybean inhibition was reduced from 75 to 55 through the use of 8.96 kg/h of the safening compound of Example 16.

Next, a treatment was run to show the safening effect of the compound of Example 16 when various amounts of Herbicide No. 3 (alachlor) were applied at a rate of 8.96 kg/h of safener. The results of this treatment have been set forth in Table XIII.

TABLE XII

| Herbicide No. | Rate of Herbicide, kg/h | Rate of Safener, kg/h | % Plant Inhibition | | | |
|---|---|---|---|---|---|---|
| | | | Sugar Beet | Grain Sorghum | Wheat | Green Foxtail |
| 3 | 4.48 | 8.96 | 100 | 90 | 95 | 100 |
| 3 | 2.24 | 8.96 | 100 | 50 | 100 | 100 |
| 3 | 1.12 | 8.96 | 80 | 20 | 99 | 100 |
| 3 | 0.56 | 8.96 | 70 | 10 | 95 | 100 |
| 3 | 4.48 | 0 | 90 | 95 | 90 | 100 |
| 3 | 2.24 | 0 | 90 | 90 | 70 | 100 |
| 3 | 1.12 | 0 | 80 | 70 | 70 | 100 |
| 3 | 0.56 | 0 | 80 | 40 | 30 | 100 |
| — | 0 | 8.96 | 0 | 0 | 0 | 0 |

It is noted from Table XIII that when the safener of Example 16 is applied at the rate of 8.96 kg/h, the safening of grain sorghum against the pernicious effect of alachlor applied at certain rates is most significant. Also, the safener does not reduce the effect of the herbicide against the undesirable green foxtail weed.

EXAMPLE 17

This Example shows the safening effect with respect to certain plants of 2-[3,5-bis(trifluoromethyl)phenoxy]-propanamide prepared in accordance with Example 10 and whose chemical structure is as follows:

TABLE XII

| Herbicide No. | Rate of Herbicide, kg/h | Rate of Safener, kg/h | % Plant Inhibition | | | | | |
|---|---|---|---|---|---|---|---|---|
| | | | Sugar Beet | Grain Sorghum | Wheat | Rice | Soybean | Corn |
| 1 | 0.56 | 0 | NP | NP | 95 | NP | NP | NP |
| 2 | 4.48 | 0 | NP | NP | NP | 90 | 75 | NP |
| 3 | 2.24 | 0 | 100 | 90 | 75 | NP | NP | NP |
| 4 | 4.48 | 0 | NP | NP | NP | 80 | NP | NP |
| 5 | 2.24 | 0 | NP | NP | NP | NP | NP | 80 |
| 1 | 0.56 | 8.96 | NP | NP | 100 | NP | NP | NP |
| 2 | 4.48 | 8.96 | NP | NP | NP | 90 | 55 | NP |
| 3 | 2.24 | 8.96 | 100 | 50 | 95 | NP | NP | NP |
| 4 | 4.48 | 8.96 | NP | NP | NP | 70 | NP | NP |
| 5 | 2.24 | 8.96 | NP | NP | NP | NP | NP | 70 |

It can be seen from Table XII that the safening compound of Example 16 significantly protects certain crops against the otherwise pernicious effect of the listed herbicides. When Herbicide No. 3 (alachlor) was applied at 2.24 kg/h, the percent grain sorghum inhibition was 90. However, this inhibition was reduced to 50% when 8.96 kg/h of the safening compound of Example 16 was used to protect against the adverse effect of the herbicide. Also significant is the fact that when

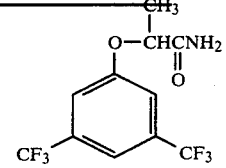

Three of the five herbicides identified in Table I were sprayed in separate treatments on the surface of soil containing various crop seeds and the percent growth inhibitions were determined. The crop identifications and the results thereof are set forth in Table XIV.

TABLE XIV

| Herbicide No. | Rate of Herbicide, kg/h | Rate of Safener, kg/h | % Plant Inhibition | | |
|---|---|---|---|---|---|
| | | | Rice | Grain Sorghum | Wheat |
| 1 | 0.56 | 0 | 99 | 95 | 97 |
| 3 | 2.24 | 0 | 97 | 97 | 90 |
| 4 | 6.72 | 0 | 97 | 97 | 90 |
| 1 | 0.56 | 8.96 | 100 | 40 | 100 |
| 3 | 2.24 | 96 | 100 | 75 | 100 |
| 4 | 6.72 | 8.96 | 100 | 70 | 90 |

It can be seen from Table XIV that the safening compound of Example 17 significantly protects grain sorghum against the otherwise pernicious effect of the three tested herbicides.

Next, a treatment was run to show the safening effect of the compound of Example 17 when various amounts of Herbicide No. 3 (alachlor) were applied at a rate of 8.96 kg/h of safener. The results of this treatment have been set forth in Table XV.

TABLE XV

| Herbicide No. | Rate of Herbicide, kg/h | Rate of Safener, kg/h | % Plant Inhibition | | |
|---|---|---|---|---|---|
| | | | Rice | Grain Sorghum | Wheat |
| 3 | 0.56 | 8.96 | 100 | 0 | 80 |
| 3 | 1.12 | 8.96 | 100 | 0 | 80 |
| 3 | 2.24 | 8.96 | 100 | 10 | 90 |
| 3 | 4.48 | 8.96 | 100 | 40 | 98 |
| 3 | 0.56 | 0 | 80 | 50 | 30 |
| 3 | 1.12 | 0 | 80 | 75 | 55 |
| 3 | 2.24 | 0 | 85 | 85 | 65 |
| 3 | 4.48 | 0 | 99 | 98 | 75 |

It is noted from Table XV that when the safener of Example 17 is applied at the rate of 8.96 kg/h, the safening of grain sorghum against the pernicious effect of alachlor applied at certain rates is most significant.

A treatment was run to show the results of pretreating the seeds with a safener and applying the herbicide to soil in which the treated seeds have been planted. Grain sorghum seeds were coated with the seed safener of Example 17 dissolved in methylene chloride. The treated seeds were dried and amounts of safener on the seeds were determined as a percent weight of seed. Both treated and untreated sorghum seeds were planted in pans containing loam soil. Selected weed species were planted in separate pans. 1.27 cm deep soil overlays were placed on each preseeded pan. Herbicide No. 3 (alachlor) was applied to the soil surface with a sprayhead. The pans were given 0.63 cm depth of overhead water, transferred to greenhouse benches and subirrigated for a period of about three weeks. The results were observed and recorded in percent growth inhibitions of each species listed.

The results of the seeds being treated before planting are shown in Table XVI.

TABLE XVI

| Herbicide No. | Rate of Herbicide, kg/h | % Safener On Seed | % Sorghum Inhibition |
|---|---|---|---|
| 3 | 0.28 | 0 | 83 |
| 3 | 1.12 | 0 | 99 |
| 3 | 4.48 | 0 | 100 |
| 3 | 0.28 | 0.125 | 0 |
| 3 | 1.12 | 0.125 | 5 |
| 3 | 4.48 | 0.125 | 33 |

Thus, it is seen from Table XVI that sorghum seeds precoated with the safener of Example 17 are protected in a significant way against the adverse effect of Herbicide No. 3 (alachlor). For example, when the sorghum seeds were precoated with 0.125 weight percent safener of Example 17 and then planted and sprayed with alachlor at the rate of 1.12 kg/h, the percent grain sorghum growth inhibition was reduced from 99 to 5.

EXAMPLE 18

This Example shows the safening effect with respect to certain plants of methyl [3,5-bis(trifluoromethyl)-phenoxy]acetate prepared in accordance with Example 6 and whose chemical structure is as follows:

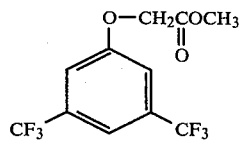

Three of the five herbicides identified in Table I were sprayed in separate treatments on the surface of soil containing various crop seeds and the percent growth inhibitions was determined. The crop identifications and the results thereof are set forth in Table XVII.

TABLE XXVII

| Herbicide No. | Rate of Herbicide, kg/h | Rate of Non-Safener, kg/h | % Plant Inhibition | | |
|---|---|---|---|---|---|
| | | | Rice | Grain Sorghum | Wheat |
| 1 | 0.56 | 0 | 98 | 98 | 95 |
| 3 | 2.24 | 0 | 98 | 98 | 75 |
| 4 | 6.72 | 0 | 90 | 100 | 90 |
| 1 | 0.56 | 8.96 | 100 | 100 | 98 |
| 3 | 2.24 | 8.96 | 100 | 100 | 100 |
| 4 | 6.72 | 8.96 | 100 | 100 | 95 |
| — | 0 | 8.96 | 90 | 90 | 80 |

It can be seen from Table XVII that the safening compound of Example 18 significantly protects grain sorghum and wheat against the otherwise pernicious effect of the three tested herbicides.

Next, a treatment was run to show the safening effect of the compound of Example 18 when various amounts of No. 3 (alachlor) were applied at a rate of 8.96 kg/h of safener. The results of this treatment have been set forth in Table XVIII.

TABLE XVIII

| Herbicide No. | Rate of Herbicide, kg/h | Rate of Safener, kg/h | % Plant Inhibition | | |
|---|---|---|---|---|---|
| | | | Green Foxtail | Grain Sorghum | Wheat |
| 3 | 0.56 | 8.96 | 90 | 0 | 60 |
| 3 | 1.12 | 8.96 | 98 | 0 | 75 |
| 3 | 2.24 | 8.96 | 100 | 20 | 70 |
| 3 | 4.48 | 8.96 | 99 | 45 | 100 |
| 3 | 0.56 | 0 | 92 | 20 | 70 |
| 3 | 1.12 | 0 | 98 | 60 | 80 |
| 3 | 2.24 | 0 | 100 | 80 | 90 |
| 3 | 4.48 | 0 | 100 | 92 | 98 |

It is noted from Table XVIII that when the safener of Example 18 is applied at the rate of 8.96 kg/h, the safener of grain sorghum against the pernicious effect of alachlor applied at certain rates is most significant. Also, the safener does not reduce the inhibition rate of the herbicide when used to control green foxtail weed.

A treatment was run to show the result of pre-treating sorghum seeds with the safener of this example and applying alachlor to the soil in which the treated seeds have been planted in accordance with the procedure above-described. The results of the seeds being treated before planting are shown in Table XIX.

TABLE XIX

| Herbicide No. | Rate of Herbicide, kg/h | % Safener on Seed | % Sorghum Inhibition |
|---|---|---|---|
| 3 | 0.28 | 0 | 95 |
| 3 | 1.12 | 0 | 99 |
| 3 | 4.48 | 0 | 100 |
| 3 | 0.28 | 0.125 | 5 |
| 3 | 1.12 | 0.125 | 18 |
| 3 | 4.48 | 0.125 | 55 |

Thus, it is seen from Table XIX that sorghum seed precoated with the safener of Example 18 are protected in a significant way against the adverse effect of Herbicide No. 3 (alachlor). For example, when the sorghum seeds were precoated with 0.125 weight percent safener of Example 18 and then planted and sprayed with alachlor at a rate of 1.12 kg/h, the percent sorghum inhibition was reduced from 99 to 18.

EXAMPLE 19

This Example shows the safening effect with respect to certain plants of N-methyl-2-[3,5-bis(trifluoromethyl)phenoxy]acetamide prepared in accordance with Example 9 and whose chemical structure is as follows:

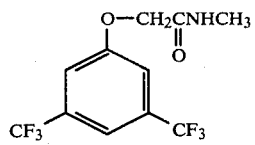

Three of the five herbicides identified in Table I were sprayed in separate treatments on the surface of soil containing various crop seeds and the percent growth inhibitions were determined. The crop identifications and the results thereof are set forth in Table XX.

TABLE XX

| Herbicide No. | Rate of Herbicide, kg/h | Rate of Safener, kg/h | % Plant Inhibition |||
|---|---|---|---|---|---|
| | | | Rice | Grain Sorghum | Wheat |
| 1 | 0.56 | 0 | 99 | 97 | 99 |
| 3 | 2.24 | 0 | 95 | 100 | 60 |
| 4 | 6.72 | 0 | 95 | 95 | 95 |
| 1 | 0.56 | 8.96 | 100 | 50 | 99 |
| 3 | 2.24 | 8.96 | 98 | 80 | 80 |
| 4 | 6.72 | 8.96 | 95 | 75 | 90 |

It can be seen from Table XX that the safening compound of Example 19 significantly protects grain sorghum against the otherwise pernicious effect of the three tested herbicides.

Next, a treatment was run to show the safening effect of the compound of Example 19 when various amounts of Herbicide No. 3 (alachlor) were applied at a rate of 8.96 kg/h. The results of this treatment have been set forth in Table XXI.

TABLE XXI

| Herbicide No. | Rate of Herbicide, kg/h | Rate of Safener, kg/h | % Plant Inhibition |||
|---|---|---|---|---|---|
| | | | Green Foxtail | Grain Sorghum | Wheat |
| 3 | 0.56 | 8.98 | 80 | 0 | 60 |
| 3 | 1.12 | 8.98 | 100 | 15 | 75 |
| 3 | 2.24 | 8.98 | 100 | 30 | 70 |
| 3 | 4.48 | 8.98 | 100 | 45 | 90 |
| 3 | 0.56 | 0 | 98 | 85 | 60 |
| 3 | 1.12 | 0 | 98 | 90 | 70 |
| 3 | 2.24 | 0 | 99 | 98 | 85 |
| 3 | 4.48 | 0 | 100 | 100 | 90 |
| — | 0 | 8.98 | 20 | 0 | 0 |

It is noted from Table XXI that when the safener of Example 19 is applied at the rate of 8.96 kg/h, the safening of grain sorghum against the pernicious effect of alachlor applied at certain rates is most significant. Also, the safener does not reduce the inhibition rate of the herbicide when used to control green foxtail weed.

EXAMPLE 20

This example shows the safening effect with respect to certain plants of ethyl [3,5-bis(trifluoromethyl)phenoxy]acetate prepared in accordance with Example 5 and whose chemical structure is as follows:

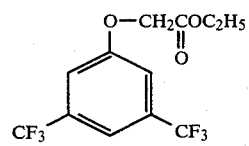

Three of the five herbicides identified in Table I were sprayed in separate treatments on the surface of soil containing various crop seeds and the percent growth inhibitions were determined. The crop identifications and the results thereof are set forth in Table XXII.

TABLE XXII

| Herbicide No. | Rate of Herbicide, kg/h | Rate of Safener, kg/h | % Plant Inhibition |||
|---|---|---|---|---|---|
| | | | Rice | Grain Sorghum | Wheat |
| 1 | 0.56 | 0 | 99 | 95 | 97 |
| 3 | 2.24 | 0 | 97 | 97 | 90 |
| 4 | 6.72 | 0 | 97 | 97 | 90 |
| 1 | 0.56 | 8.96 | 99 | 10 | 95 |
| 3 | 2.24 | 8.96 | 100 | 50 | 75 |
| 4 | 6.72 | 8.96 | 95 | 60 | 60 |

It can be seen from Table XXII that the safening compound of Example 20 significantly protects grain sorghum against the otherwise pernicious effect of the three tested herbicides.

Next, a treatment was run to show the safening effect of the compound of Example 20 when various amounts of Herbicide No. 3 (alachlor) were applied at a rate of 8.96 kg/h of safener. The results of this treatment have been set forth in Table XXIII.

TABLE XXIII

| Herbicide No. | Rate of Herbicide, kg/h | Rate of Safener, kg/h | % Plant Inhibition ||
|---|---|---|---|---|---|
| | | | Rice | Grain Sorghum | Wheat |
| 3 | 0.56 | 8.96 | 70 | 0 | 30 |
| 3 | 1.12 | 8.96 | 75 | 0 | 45 |
| 3 | 2.24 | 8.96 | 85 | 0 | 30 |
| 3 | 4.48 | 8.96 | 85 | 20 | 60 |
| 3 | 0.56 | 0 | 80 | 50 | 30 |
| 3 | 1.12 | 0 | 80 | 75 | 55 |

TABLE XXIII-continued

| Herbicide No. | Rate of Herbicide, kg/h | Rate of Safener, kg/h | % Plant Inhibition | | |
|---|---|---|---|---|---|
| | | | Rice | Grain Sorghum | Wheat |
| 3 | 2.24 | 0 | 85 | 85 | 65 |
| 3 | 4.48 | 0 | 99 | 98 | 75 |
| — | 0 | 8.96 | 0 | 0 | 0 |

It is noted from Table XXIII that when the safener of Example 20 is applied at the rate of 8.96 kg/h, the safening of grain sorghum against the pernicious effect of alachlor applied at certain rates is most significant.

A treatment was run to show the result of pretreating sorghum seeds with the safener of this example and applying alachlor to the soil in which the treated seeds have been planted in accordance with the procedure above described. The results of the seeds being treated with safener before planting is shown in Table XXIV.

TABLE XXIV

| Herbicide No. | Rate of Herbicide, kg/h | % Plant Inhibition | |
|---|---|---|---|
| | | % Safener on Seed | % Sorghum Inhibition |
| 3 | 0.28 | 0 | 83 |
| 3 | 1.12 | 0 | 99 |
| 3 | 4.48 | 0 | 100 |
| 3 | 0.28 | 0.125 | 5 |
| 3 | 1.12 | 0.125 | 5 |
| 3 | 4.48 | 0.125 | 13 |

Thus, it is seen from Table XXIV that grain sorghum seeds precoated with the safener of Example 20 are protected in a significant way against the adverse effect of Herbicide No. 3 (alachlor). For example, when the sorghum seeds were precoated with 0.125 weight percent of Example 20 and then planted and sprayed with alachlor at a rate of 1.12 kg/h, the percent sorghum inhibition was reduced from 99 to 5.

EXAMPLE 21

This Example shows the safening effect with respect to 2-[3,5-bis(trifluoromethyl)phenoxy]acetamide prepared in accordance with Example 8 and whose chemical structure is as follows:

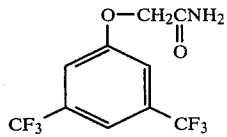

Three of the five herbicides identified in Table I were sprayed in separate treatments on the surface of soil containing various crop seeds and the percent growth inhibitions were determined. The crop identifications and the results thereof are set forth in Table XXV.

TABLE XXV

| Herbicide No. | Rate of Herbicide, kg/h | Rate of Safener, kg/h | % Plant Inhibition | | |
|---|---|---|---|---|---|
| | | | Rice | Grain Sorghum | Wheat |
| 1 | 0.56 | 0 | 97 | 85 | 99 |
| 3 | 2.24 | 0 | 90 | 75 | 60 |
| 4 | 6.72 | 0 | 90 | 95 | 90 |
| 1 | 0.56 | 8.96 | 98 | 40 | 96 |
| 3 | 2.24 | 8.96 | 95 | 40 | 70 |
| 4 | 6.72 | 8.96 | 90 | 60 | 50 |

It can be seen from Table XXV that the safening compound of Example 21 significantly protects grain sorghum against the otherwise pernicious effect of the three tested herbicides.

Next, a treatment was run to show the safening effect of the compound of Example 21 when various amounts of Herbicide No. 3 (alachlor) were applied at a rate of 8.96 kg/h of safener. The results of this treatment have been set forth in Table XXVI.

TABLE XXVI

| Herbicide No. | Rate of Herbicide, kg/h | Rate of Safener, kg/h | % Plant Inhibition | | |
|---|---|---|---|---|---|
| | | | Green Foxtail | Grain Sorghum | Wheat |
| 3 | 0.56 | 8.98 | 98 | 0 | 50 |
| 3 | 1.12 | 8.98 | 100 | 20 | 55 |
| 3 | 2.24 | 8.98 | 98 | 40 | 70 |
| 3 | 4.48 | 8.98 | 100 | 70 | 75 |
| 3 | 0.56 | 0 | 95 | 70 | 35 |
| 3 | 1.12 | 0 | 98 | 80 | 40 |
| 3 | 2.24 | 0 | 98 | 85 | 65 |
| 3 | 4.48 | 0 | 99 | 90 | 85 |
| — | 0 | 8.98 | 0 | 0 | 0 |

It is noted from Table XXVI that when the safener of Example 21 is applied at the rate of 8.96 kg/h, the safening of grain sorghum against the pernicious effect of alachlor applied at certain rates is most significant. Also, the safener does not reduce the inhibition rate of the herbicide when used to control green foxtail weed.

EXAMPLE 22

This Example shows the safening effect with respect to the sodium salt of [3,5-bis(trifluoromethyl)phenoxy]acetic acid prepared in accordance with Example 11 and whose chemical structure is as follows:

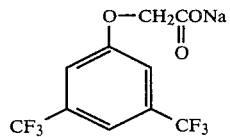

Herbicide No. 3 (alachlor) was sprayed on planted wheat at an application rate of 2.24 kg/h. It was found that the inhibition of wheat growth was 85% when the herbicide was used. However, when the same herbicide was used in sequential application of 8.96 kg/h of the safener of this Example, the inhibition of wheat growth was reduced to 65%.

EXAMPLE 23

This Example shows the non-safening effect of methyl[3-trifluoromethyl)phenoxy]acetate whose chemical formula is as follows:

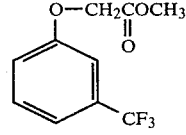

Three of the five herbicides identified in Table I were sprayed in separate treatments on the surface of soil containing various crop seeds and the percent growth inhibitions were determined. The crop identifications and the results thereof are set forth in Table XXVII.

TABLE XXVII

| Herbicide No. | Rate of Herbicide, kg/h | Rate of Non-Safener, kg/h | % Plant Inhibition Rice | Grain Sorghum | Wheat |
|---|---|---|---|---|---|
| 1 | 0.56 | 0 | 98 | 98 | 95 |
| 3 | 2.24 | 0 | 98 | 98 | 75 |
| 4 | 6.72 | 0 | 90 | 100 | 90 |
| 1 | 0.56 | 8.96 | 100 | 100 | 98 |
| 3 | 2.24 | 8.96 | 100 | 100 | 100 |
| 4 | 6.72 | 8.96 | 100 | 100 | 95 |
| — | 0 | 8.96 | 90 | 90 | 80 |

It can be seen from Table XXVII that the compound of Example 23 instead of safening crop seeds against the three applied herbicides acts as a herbicide itself by augmenting the pernicious effect of the three herbicides.

EXAMPLE 24

This Example shows the non-safening effect of N-methyl-2-[3-(trifluoromethyl)phenoxy]acetamide whose chemical formula is as follows:

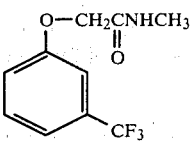

Three of the five herbicides identified in Table I were sprayed in separate treatments on the surface of soil containing various crop seeds and the percent growth inhibition was determined. The crop seed identifications and the results thereof are set forth in Table XXVIII.

TABLE XXVIII

| Herbicide No. | Rate of Herbicide, kg/h | Rate of Non-Safening, kg/h | % Plant Inhibition Rice | Grain Sorghum | Wheat |
|---|---|---|---|---|---|
| 1 | 0.56 | 0 | 99 | 95 | 99 |
| 3 | 2.24 | 0 | 99 | 98 | 75 |
| 4 | 6.72 | 0 | 95 | 97 | 95 |
| 1 | 0.56 | 8.96 | 100 | 100 | 99 |
| 3 | 2.24 | 8.96 | 100 | 100 | 100 |
| 4 | 6.72 | 8.96 | 99 | 100 | 95 |

It can be seen from Table XXVIII that the compound of Example 24 instead of safening the crop seeds against the three applied herbicides acts as a herbicide itself by augmenting the pernicious effect of the three herbicides.

The above examples illustrate that the bis-trifluoromethylphenoxycarboxylic acid compounds of the present invention are useful in reducing herbicidal injury to crop plants, especially grain sorghum. As indicated above, the safening agents may be applied to the plant locus as a mixture, i.e., a mixture of a herbicidally effective amount of herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 25:1 (preferably 1:5 to 5:1) parts by weight may be employed.

The amount of herbicide employed in the practice of the present invention will be at least an effective herbicidal amount. In general, effective herbicidal amounts are in the range of 0.2 and 12 kilograms/hectare. The preferred range of rate of application is from 0.4 to about 10 kg/h. It will be appreciated that at times amounts either below or above these ranges will be necessary to obtain the best results. The selection of the herbicide to inhibit the growth of seedling weeds and the emergence of weeds depends upon the specifics of the weed and the identity and the amounts of the herbicide applied.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fuller's earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, hand-carried or tractor-mounted spreaders, power dusters, boom and hand sprayers, spray dusters and graunular applicators. The compositions can also be applied from aircraft as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, smaller amounts of safening agent are required to treat such seeds. A weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the compound preferably is formulated as a powder, emulsifiable concentrate solution or flowable formulation which can be diluted with water by the seed treater for use in the seed treating apparatus. Of couse, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher alkylarylsulfonates such as sodium dodecylbenzenesulfonate and the sodium salts of alkylnapthalenesulfonaic acids, fatty alcohol sulfates such as the sodium salts of monoesters or sulfuric acid with n-aliphatic alcohols containing 8-18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long chain alcohols usually containing 10-18 carbon atoms, and condensation products of alkylene oxide with fatty acids, alkylphenols and mercaptans.

The following examples illustrate the preparation of commercial seed treating compositions of the present invention:

EXAMPLES 25-29

The ingredients set forth in Table XXIX are blended to form an emulsifiable concentrate. The resulting mixture after proper dilution can be applied to plant loci where safening of such plants against the adverse effects of weed herbicide is desired. The ingredients are given as weight percents.

TABLE XXIX

| Ingredients | Example 25 | Example 26 | Example 27 | Example 28 | Example 29 |
|---|---|---|---|---|---|
| Safener of Ex. 9 | | | | | 30.0 |
| Safener of Ex. 5 | 60.0 | | | | |
| Safener of Ex. 6 | | 25.0 | | | |
| Safener of Ex. 7 | | | 42.0 | | |
| Safener of Ex. 2 | | | | 37.0 | |
| Calcium dodecylbenzene sulfonate | 3.5 | 2.0 | 2.3 | 2.1 | 2.5 |
| Nonylphenolpropylethylene ether | 2.0 | 3.0 | 1.2 | | 2.0 |
| Castor oil polyoxyethylene ether | 0.5 | | 1.5 | 1.9 | 2.5 |
| Xylene | 34.0 | 60.0 | 53.0 | 59.0 | 33.0 |
| Monochlorobenzene | | 10.0 | | | |
| Chloroform | | | | | 30.0 |

EXAMPLES 29-34

In the preparation of seed safening composition in accordance with these examples, the active safener is added slowly to the aqueous base material with controlled agitation and cooling followed by the addition thereto of the surfactant where employed. The resulting water-soluble concentrates are sprayed to the plant loci as such or after dilution with water with or without additional surfactant. The ingredients used in these examples and their weight percent are set forth in Table XXX.

TABLE XXX

| Ingredients | Ex. 29 | Ex. 30 | Ex. 31 | Ex. 32 | Ex. 33 | Ex. 34 |
|---|---|---|---|---|---|---|
| Safener of Ex. 1 | 25.0 | | | 25.0 | | |
| Safener of Ex. 3 | | 35.0 | | | 35.0 | |
| Safener of Ex. 4 | | | 30.0 | | | 30.0 |
| Isopropylamine | 5.2 | 7.2 | | 5.2 | 7.2 | |
| Potassium hydroxide (85%) | | | 6.3 | | | 6.3 |
| Ethoxylated soyamine | | | | 3.0 | 3.5 | 2.5 |
| Water | 69.8 | 57.8 | 63.7 | 66.8 | 54.3 | 61.2 |

EXAMPLE 35

98 parts of the safener of Example 11 is suitably blended with 2 parts of Aerosol OTB which is a composition of sodium dioctylsulfosuccinate and benzoic acid. The resulting mixture is a water soluble powder which can be added to water with or without added surfactant to give a solution suitable for applying to plant loci where safening of such plants against the adverse effects of weed herbicide is desired.

EXAMPLES 36 AND 37

The ingredients set forth in Table XXXI are blended and ground using a media mill to prepare flowable safening formulations.

TABLE XXXI

| Ingredients | Example 36 | Example 37 |
|---|---|---|
| Safener of Example 8 | 25.0 | 42.0 |
| Tween 65 | 3.0 | |
| Dodecylphenolpolyethylene ether | 1.5 | |
| Sodium lignosulfonate | | 3.5 |
| Sodium -methyl- -oleyl taurate | | 2.0 |
| Silica aerogel | | 1.5 |
| Water | | 51.0 |
| Light mineral oil | 70.5 | |

EXAMPLES 38 AND 39

The ingredients set forth in Table XXXII are blended and then ground together to provide a fine wettable powder suitable for dilution and for applying to plant loci where safening of such plants against the adverse effects of weed herbicide is desired.

TABLE XXXII

| Ingredients | Example 38 | Example 39 |
|---|---|---|
| Safener of Example 9 | 80.0 | 5.0 |
| Sodium lignosulfonate | 2.5 | |
| Igepon T-73 | 3.5 | |
| Aerosol OTB | | 1.0 |
| Amorphous silica | 14.0 | |
| Kaolin | | 94.0 |

What is claimed is:

1. A method of reducing injury to crop plants due to the application thereto of at least one weed herbicide which comprises applying to the plant locus a safening effective amount of at least one compound having the structural formula:

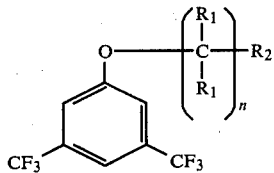

wherein $R_1$ is independently selected from the group consisting of hydrogen and $C_1-C_5$ alkyl, n is a whole number of 1-5, inclusive, and $R_2$ is selected from the group consisting of

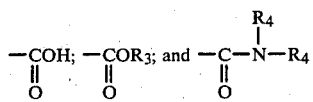

wherein $R_3$ is selected from the group consisting of $C_1-C_5$ alkyl and agriculturally acceptable cations and $R_4$ is independently selected from the group consisting of hydrogen and $C_1-C_5$ alkyl.

2. A method of reducing injury to grain sorghum due to the application thereto of at least one acetanilide herbicide which comprises applying to the plant locus a safening effective amount of at least one compound having the structural formula

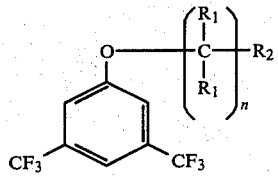

wherein $R_1$ is independently selected from the group consisting of hydrogen and $C_1-C_5$ alkyl, n is a whole number of 1-5, inclusive, and $R_2$ is selected from the group consisting of

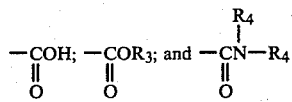

wherein $R_3$ is selected from the group consisting of $C_1-C_5$ alkyl and alkali metal cations and $R_4$ is independently selected from the group consisting of hydrogen and $C_1-C_5$ alkyl.

3. The method of claim 1 wherein the herbicide is selected from the group consisting of 2-chloro-2',6'-diethyl-N-(methoxymethyl)acetanilide; 2-chloro-2',6'-diethyl-N-(butoxymethyl) acetanilide; 2,3,3-trichloroallyl diisopropylthiocarbamate; 2-chloro-4-ethylamino-6-isopropylamino-1,3,5 triazine; and 2-chloro-2'-methyl-6'-methoxy-N-(isopropyl)acetanilide; and wherein the safening compound is selected from the group consisting of 4-[3,5-bis(trifluoromethyl)phenoxy]butanoic acid;
ethyl 4-[3,5-bis(trifluoromethyl)phenoxy]butyrate;
2-[3,5-bis(trifluoromethyl)phenoxy]propionic acid;
[3,5-bis(trifluoromethyl)phenoxy]acetic acid;
methyl [3,5-bis(trifluoromethyl)phenoxy]acetate;
2-[3,5-bis(trifluoromethyl)phenoxy]propanamide;
ethyl [3,5-bis(trifluoromethyl)phenoxy]acetate;
N-methyl 2-[3,5-bis(trifluoromethyl)phenoxy]acetamide;
2-[3,5-bis(trifluoromethyl)phenoxy]acetamide;
sodium salt of [3,5-bis(trifluoromethyl)phenoxy]acetic acid;
and ethyl 2-[3,5-bis(trifluoromethyl)phenoxy]propionate.

4. A method of reducing injury to grain sorghum due to the application thereto of an acetanilide herbicide which comprises applying to the plant locus a safening effective amount of [3,5-bis(trifluoromethyl)phenoxy]acetic acid.

5. A method of reducing herbicidal injury to food crop plants which comprises applying to the plant locus an effective amount of a mixture comprising a herbicidally effective amount of at least one weed herbicide and a safening effective amount of at least one compound having the formula

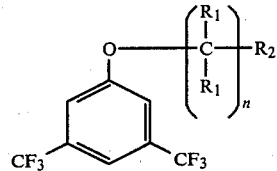

wherein $R_1$ is independently selected from the group consisting of hydrogen and $C_1-C_5$ alkyl, n is a whole number of 1-5, inclusive, and $R_2$ is selected from the group consisting of

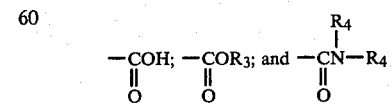

wherein $R_3$ is selected from the group consisting of $C_1-C_5$ alkyl and alkali metal cations and $R_4$ is independently selected from the group consisting of hydrogen and $C_1-C_5$ alkyl.

6. The method of claim 5 wherein the weed herbicide is selected from the group consisting of 2-chloro-2',6'-diethyl-N-(methoxymethyl)acetanilide; 2-chloro-2-',6'-diethyl-N-(butoxymethyl)acetanilide; 2,3,3-trichloroallyl diisopropylthiocarbamate; 2-chloro-4-ethylamino-6-isopropylamino-1,3,5-triazine; and 2-chloro-2'-methyl-6'-methoxy-N-(isopropyl)acetanilide and wherein the safening compound is selected from the group consisting of 4-[3,5-bis(trifluoromethyl)phenoxy]butanoic acid;
ethyl 4-[3,5-bis(trifluoromethyl)phenoxy]butyrate;
2-[3,5-bis(trifluoromethyl)phenoxy]propionic acid;
[3,5-bis(trifluoromethyl)phenoxy]acetic acid;
methyl [3,5-bis(trifluoromethyl)phenoxy]acetate;
2-[3,5-bis(trifluoromethyl)phenoxy]propanamide;
ethyl [3,5-bis(trifluoromethyl)phenoxy]acetate;
N-methyl-2-[3,5-bis(trifluoromethyl)phenoxy]acetamide;
2-[3,5-bis(trifluoromethyl)phenoxy]acetamide;
sodium salt of [3,5-bis(trifluoromethyl)phenoxy]acetic acid;
and ethyl 2-[3,5-bis(trifluoromethyl)phenoxy]propionate.

7. A method of reducing herbicidal injury to food crop plants by the application of at least one weed herbicide which comprises coating food crop seeds prior to planting thereof with a safening effective amount of at least one compound having the formula:

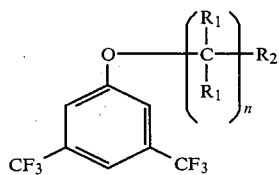

wherein $R_1$ is independently selected from the group consisting of hydrogen and $C_1$–$C_5$ alkyl, n is a whole number of 1–5, inclusive, and $R_2$ is selected from the group consisting of

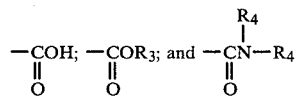

wherein $R_3$ is selected from the group consisting of $C_1$–$C_5$ alkyl and alkali metal cations and $R_4$ is independently selected from the group consisting of hydrogen and $C_1$–$C_5$ alkyl.

8. The method of claim 7 wherein the herbicide is an acetanilide herbicide and the food crop seed is grain sorghum.

9. The method of claim 7 wherein the weed herbicide is selected from the group consisting of 2-chloro-2',6'-diethyl-N-(methoxymethyl)acetanilide; 2-chloro-2',6'-diethyl-N-(butoxymethyl)acetanilide; 2,3,3-trichloroallyldiisopropylthiocarbamate; 2-chloro-4-ethylamino-6-isopropylamino-1,3,5 triazine; and 2-chloro-2'-methyl-6'-methoxy-N(isopropyl)acetanilide and wherein the safening compound is selected from the group consisting of 4-[3,5-bis(trifluoromethyl)phenoxy]butanoic acid;
ethyl 4-[3,5-bis(trifluoromethyl)phenoxy]butyrate;
2-[3,5-bis(trifluoromethyl)phenoxy]propionic acid;
[3,5-bis(trifluoromethyl)phenoxy]acetic acid;
methyl [3,5-bis(trifluoromethyl)phenoxy]acetate;
2-[3,5-bis(trifluoromethyl)phenoxy]propanamide;
ethyl [3,5-bis(trifluoromethyl)phenoxy]acetate;
N-methyl-2-[3,5-bis(trifluoromethyl)phenoxy]acetamide;
2-[3,5-bis(trifluoromethyl)phenoxy]acetamide;
sodium salt of [3,5-bis(trifluoromethyl)phenoxy]acetic acid;
and ethyl 2-[3,5-bis(trifluoromethyl)phenoxy]propionate.

10. A mixture which comprises a herbicidally effective amount of at least one weed herbicide and a safening effective amount of at least one compound having the formula:

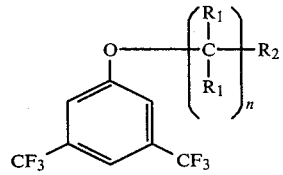

wherein $R_1$ is independently selected from the group consisting of hydrogen and $C_1$–$C_5$ alkyl, n is a whole number of 1–5, inclusive, and $R_2$ is selected from the group consisting of

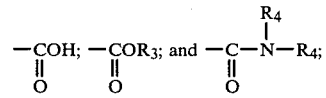

wherein $R_3$ is selected from the group consisting of $C_1$–$C_5$ alkyl and alkali metal cations and $R_4$ is independently selected from the group consisting of hydrogen and $C_1$–$C_5$ alkyl.

11. The mixture of claim 10 wherein the weed herbicide is selected from the group consisting of
2-chloro-2',6'-diethyl-N-(methoxymethyl)acetanilide;
2-chloro-2',6'-diethyl-N-(butoxymethyl)acetanilide;
2,3,3-trichloroallyldiisopropylthiocarbamate;
2-chloro-4-ethylamino-6-isopropylamino-1,3,5-triazine;
and 2-chloro-2'-methyl-6'-methoxy-N(isopropyl)acetanilide
and wherein the safening compound is selected from the group consisting of
4-[3,5-bis(trifluoromethyl)phenoxy]butanoic acid;
ethyl 4-[3,5-bis(trifluoromethyl)phenoxy]butyrate;
2-[3,5-bis(trifluoromethyl)phenoxy]propionic acid;
[3,5-bis(trifluoromethyl)phenoxy]acetic acid;
methyl [3,5-bis(trifluoromethyl)phenoxy]acetate;
2-[3,5-bis(trifluoromethyl)phenoxy]propanamide;
ethyl [3,5-bis(trifluoromethyl)phenoxy]acetate;
N-methyl-2-[3,5-bis(trifluoromethyl)phenoxy]acetamide;
2-[3,5-bis(trifluoromethyl)phenoxy]acetamide;
sodium salt of [3,5-bis(trifluoromethyl)phenoxy]acetic acid;
and ethyl 2-[3,5-bis(trifluoromethyl)phenoxy]propionate.

12. A food crop seed, the plants grown from which are rendered resistant to injury due to weed herbicides, coated with a safening effective amount of a compound having the formula:

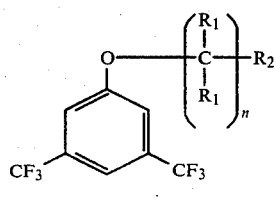

wherein $R_1$ is independently selected from the group consisting of hydrogen and $C_1$–$C_5$ alkyl, n is a whole number of 1–5, inclusive, and $R_2$ is selected from the group consisting of

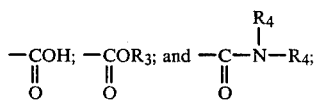

wherein $R_3$ is selected from the group consisting of $C_1$–$C_5$ alkyl and alkali metal cations and $R_4$ is independently selected from the group consisting of hydrogen and $C_1$–$C_5$ alkyl.

13. The grain sorghum seed of claim 12.

* * * * *

UNITED STATES PATENT AND TRADEMARK OFFICE
CERTIFICATE OF CORRECTION

PATENT NO. : 4,416,687             Page 1 of 2

DATED : November 22, 1983

INVENTOR(S) : John J. D'Amico and Tann R. Schafer

It is certified that error appears in the above-identified patent and that said Letters Patent are hereby corrected as shown below:

Column 1, line 41 - delete "of"

Column 1, line 41 - delete "bis(trifluoromehtyl)phenoxy" and insert --bis(trifluoromethyl)phenoxy--

Column 14, line 13 - delete "Hericide" and insert --Herbicide--

Column 20, Table XXVII - delete "XXVII" and insert --XVII--

Column 26, line 60 - delete "graunular" and insert --granular--

UNITED STATES PATENT AND TRADEMARK OFFICE
CERTIFICATE OF CORRECTION

PATENT NO. : 4,416,687

DATED : November 22, 1983

INVENTOR(S) : John J. D'Amico and Tann R. Schafer

It is certified that error appears in the above-identified patent and that said Letters Patent are hereby corrected as shown below:

Columns 11-12, Table III, Herbicide No. column - line 2:
    delete "2" and insert --3--

Column 12, Table V, Grain Sorghum column - line 1:
    delete "20" and insert --10--

Column 18, Table XII: delete "XII" and insert --XIII--

Signed and Sealed this

Sixth Day of March 1984

[SEAL]

Attest:

GERALD J. MOSSINGHOFF

Attesting Officer

Commissioner of Patents and Trademarks